United States Patent [19]

Hofstein

[11] 4,200,885
[45] Apr. 29, 1980

[54] ULTRASONIC SCOPE

[75] Inventor: Steven R. Hofstein, Princeton, N.J.

[73] Assignee: Princeton Electronic Products, Inc., North Brunswick, N.J.

[21] Appl. No.: 956,899

[22] Filed: Nov. 2, 1978

[51] Int. Cl.² .............................................. H04N 7/18
[52] U.S. Cl. ..................................... 358/112; 128/660
[58] Field of Search ............... 358/110, 111, 112, 113, 358/231, 237, 238, 239; 128/660, 661, 662, 663; 358/254

[56] References Cited

U.S. PATENT DOCUMENTS

| | | | |
|---|---|---|---|
| 4,099,179 | 7/1978 | Hofstein | 358/112 |
| 4,121,250 | 10/1978 | Huelsman | 358/112 |
| 4,156,304 | 5/1979 | Lee | 128/660 |

Primary Examiner—Robert L. Griffin
Assistant Examiner—Michael A. Masinick
Attorney, Agent, or Firm—Ostrolenk, Faber, Gerb & Soffen

[57] ABSTRACT

An ultrasonic display apparatus which utilizes novel electrical and optical means to produce an image which is spatially superimposed within the exact area of the patient's body being scanned is disclosed. The ultrasonic display apparatus includes a cathode ray tube, a planar mirror and a transducer which are mounted within a housing having a viewing window formed therein. The cathode ray tube includes a generally planar viewing face which lies in a first plane. The planar mirror lies in a second plane. One of the mirror and cathode ray tube is pivotally mounted within the housing such that the angle between the first and second planes is adjustable. The transducer is pivotally mounted in the housing and is connected to electric circuit means which cause the transducer to generate a succession of ultrasonic beams which propagate along a third plane. Angle adjustment means are provided for adjusting the angle of the third plane with respect to the housing. The angle adjustment means also maintains the angle between the second and third planes equal to the angle between the first and second planes when the angle of the third plane is changed with respect to the housing.

11 Claims, 4 Drawing Figures

ULTRASONIC SCOPE

BACKGROUND OF THE INVENTION

The present invention relates to ultrasonic systems of the pulse echo type which are particularly suited for use in medical diagnosis. Ultrasonic systems are in use today and serve as an excellent tool in obtaining graphic displays of body internal configuration. A conventional system includes a transmitter, an ultrasonic transducer, a receiver, and a display unit.

In use, the transducer is positioned at the skin, the transmitter provides an ultrasonic pulse to the transducer which in turn launches an ultrasonic pulse into the body. The echoes produced by various discontinuities in the body (such as variations in the density of internal organs) are picked up by the transducer, converted into electrical signals and sent to the receiver which in turn provides signals to the display unit.

The transducer may be moved along the surface of the body and the angle of orientation of the transducer may be changed to scan a complete section through the body, with the resultant picture having something of an appearance of an x-ray picture. Ultrasonic systems of the foregoing type are divided into two primary categories; those providing a still frame display and those providing a real time display.

Those systems providing a still or frozen display utilize a B-contact scanner which require that the operator of the unit move the probe to "accumulate" the image for viewing. The resultant image is a form of snapshot or "still picture" which the physician can later use to diagnose various patient conditions. The real type systems utilize mechanical or spatial electronic means to move the beam of sound energy across the patient's body without actual motion by the examiner. Those systems utilizing special electronic means utilize an elongated bar having a large plurality of small transducers embedded therein. By sequentially pulsing the transducers, it is possible to electronically scan an entire "slice" of the patient's body without moving the elongated bar. In those systems utilizing mechanical means, a single small probe is rapidly pivoted in an arc which causes the sonic beams transmitted by the transducer to traverse an entire "slice" of the patient's body. In this case, the viewer shows a conical image rather than a square image, with the point of the conical image extending from the pivot point of the transducer.

In each of the foregoing systems, the ultrasonic pulse generated by the transducer is reflected from the various discontinuities in the body and are returned along the propagation path to the originating transducer. The intensity of the echo is proportional to the density and size of the reflecting object and the time delay between the initial transmitted pulse and the return echo is proportional to the distance between the source of the transmitted pulse and the reflecting object.

A major difficulty which is encountered in obtaining a suitable display of the return echo information in such systems is the fact that the format of the returned echo information is different from that of the format of the television Raster type display. The echo information may be different from the television display requirements in two primary parameters; spatial and time. The spatial parameters are at odds when the echo signal is in a conical form (such as that received when using a pivoting transducer) and the television information is in the standard Raster type rectangular form. The time parameters vary due to the fact that a typical scan rate of the transducer (as high as one-fifth of a second) is substantially slower than the required scan rate for the TV display (typically 30 frames per second). Slower scan rates produce an undesirable "flicker" in the TV display.

To overcome the foregoing problems, the prior art utilizes a scan converter for receiving and storing the incoming data from the receiver while in a write mode and for providing a video signal to the TV monitor tube during the read mode. A suitable scan converter for this purpose is disclosed in U.S. Pat. No. 4,099,179 issued in the name of Steven R. Hofstein and assigned to the assignee of the present invention. The specification of the foregoing patent is incorporated herein by reference.

The primary advantage of ultrasonic scanning systems over the more common x-ray system, is the safety of the ultrasonic systems. The hazards of x-radiation are well known and need not be reviewed herein. This hazard is overcome by the use of the relatively safe ultrasonic signals generated by the ultrasonic transducer. The major drawback of the ultrasonic systems are their relative lack of clarity. While the display provided by ultrasonic systems provide a useful indication of the general shape and structure of internal organs, the definition of the visual displays provided by such systems is not extremely high. Accordingly, it is necessary for the physician utilizing the ultrasonic system to know what portion of the body he is scanning in order to properly interpret the video information provided on the television display. That is, the physician must know which organ or organs he is scanning to properly interpret the visual display. Which organ is being scanned at any given instant is a function of both the location of the transducer relative to the patient's body and the angle of propagation of the sonic signals. Thus, the physician must know both the position of the transducer and its angle relative to the patient.

For this reason, it has been necessary for specially trained physicians to utilize the ultrasonic scanning apparatus. While these individuals have become very adept at interpreting what "slice" of the body the probe is scanning, this requirement has made the ultrasonic probe impractical for general use by physicians.

BRIEF SUMMARY OF THE INVENTION

A primary object of the present invention is to overcome the foregoing drawbacks utilizing novel electronic and optical means which produce an image which is spatially superimposed within the exact area of the patient's body being scanned. In accordance with this system, the image which is viewed by the physician lies exactly in the plane in which the sonic signals are generated in the patient's body. This gives the physician the illusion that he is actually looking into the patient's body along a section corresponding to the plane of the ultrasonic signals. As a result, the physician need not interpret what position the probe is actually scanning within the body of the patient, since the optics of the present invention provide him with this information.

The foregoing and other objects of the present invention are obtained by providing an ultrasonic display apparatus comprising:

a housing having a viewing window formed therein;

a cathode ray tube mounted in said housing, said cathode ray tube including a generally planar viewing face lying in a first plane;

a planar mirror mounted in said housing and lying in a second plane, one of said mirror and cathode ray tube being pivotally mounted such that the angle between said first and second planes is adjustable;

a transducer pivotally mounted in said housing;

electronic circuit means for causing said transducer to generate a succession of ultrasonic beams which propagate along a third plane; said electronic circuit means also for processing ultrasonic echo signals received by said transducer and for causing said cathode ray tube to display a real time Raster type image corresponding to the information contained in said ultrasonic echo signals; and angle adjustment means for adjusting the angle of said third plane with respect to said housing, said angle adjustment means also for maintaining the angle between said second and third planes equal to the angle between said first and second planes when said angle of said third plane is changed with respect to said housing.

BRIEF DESCRIPTION OF THE DRAWINGS

For the purpose of illustrating the invention, there is shown in the drawing a form which is presently preferred; it being understand, however, that this invention is not limited to the precise arrangements and instrumentalities shown.

DETAILED DESCRIPTION OF THE INVENTION

Figure 1:
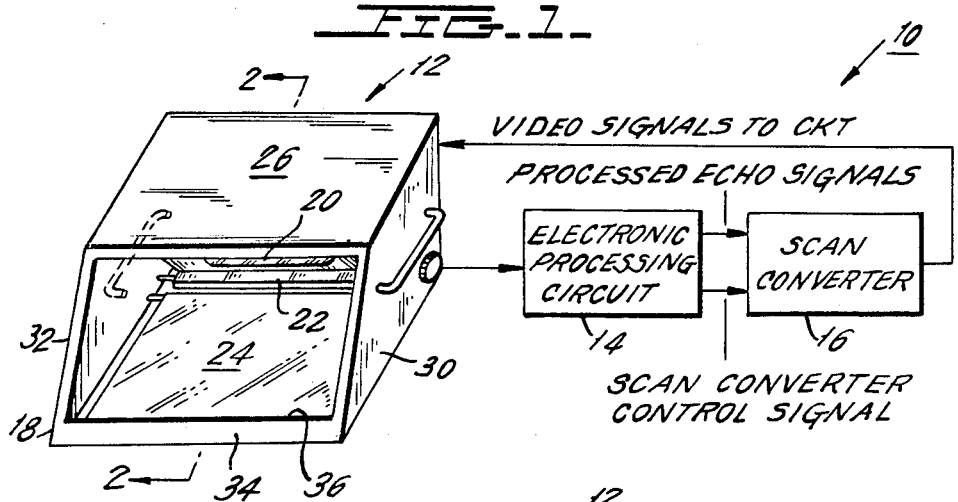
FIG. 1 is a schematic diagram of the ultrasonic scanning system of the present invention.

Referring now to the drawings wherein unlike numerals indicate like elements, there is shown in FIG. 1 a schematic diagram of an ultrasonic scanning system constructed in accordance with the principals of the present invention and designated generally as 10. Ultrasonic scanning system 10 includes an image display box 12, an electronic processing circuit 14 and a scan converter 16. Image display box 12 includes a housing 18, a cathode ray tube (hereinafter CRT) 20, a transducer 22 and a mirror 24.

Figure 2:
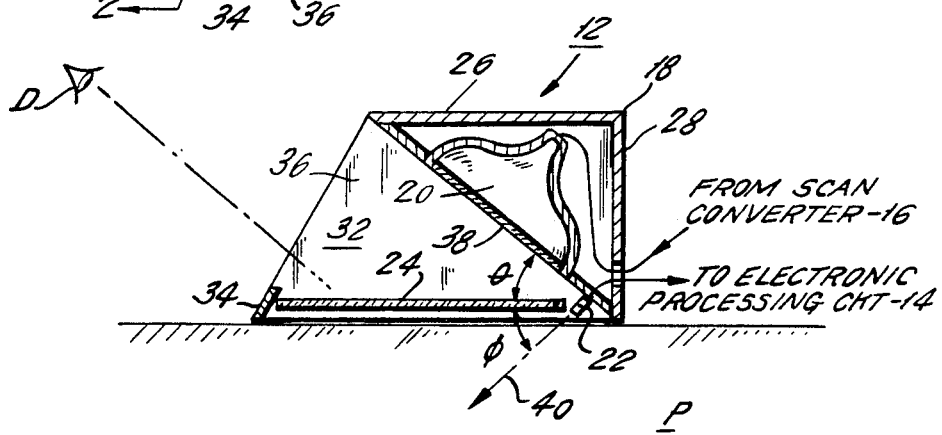
FIG. 2 is a cross-sectional view taken along line 2—2 of FIG. 1.

As best seen in FIGS. 1 and 2, housing 18 includes a top wall 26, a rear wall 28, a pair of side walls, 30, 32 and a front wall 34. A viewing window 36 is formed in the front wall 34. As best seen in FIG. 2, the front wall 34 preferably slopes downwardly from the top wall 26 to permit the physician to look through the viewing window 36 at an angle with respect to the mirror 24.

Figures 3, 4:
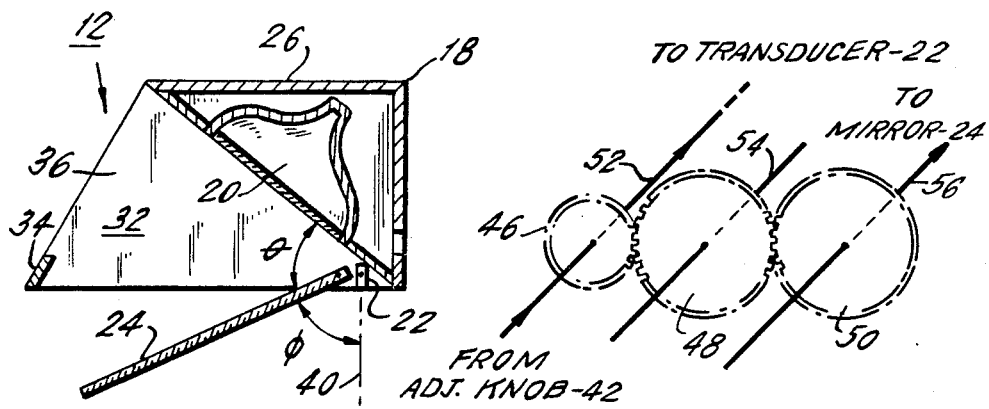
FIG. 3 is a second cross-sectional view of the image display box of FIG. 1.
FIG. 4 is a schematic diagram of angle adjustment gears which form part of the image display box of the present invention.

The mirror 24 is preferably a half silvered mirror which is pivotally connected to the side walls 30, 32 of housing 18. As will be explained below, mirror 24 is preferably pivotable between a first position wherein it is parallel with the top wall 26 of housing 18 and a second position wherein it extends below the bottom of housing 18 as shown in FIG. 3. Alternatively, the mirror 24 may be stationarily mounted along the bottom of housing 18 and the CRT 20 may be made pivotable with respect thereto. The important limitation is that the angle $\theta$ between the generally planar viewing face 38 of CRT 20 and the planar mirror 24 is adjustable.

In the embodiment illustrated, transducer 22 is shown as a bar transducer of the type which comprises a plurality of spaced transducers which are sequentially pulsed by the electronic processing circuit 24. Alternatively, transducer 22 may be replaced by a single mechanically pivoting transducer. In either case, the transducer 22 is energized in such a manner that the transducer 22 generates a plurality of ultrasonic beams 40 which propagates along a single plane determined by the angle of orientation of transducer 22 with respect to housing 18. The angle of orientation of transducer 22 with respect to housing 18 is controlled by a rotatable knob 42 so as to determine the angle at which the ultrasonic beams 40 enter the body of the patient. For reasons which will become apparent below, it is desirable to maintain the angle $\theta$ between the mirror 24 and the viewing face 38 of CRT 20 equal to the angle $\phi$ between the mirror 24 and the ultrasonic beams 40 for all orientations of transducer 22. To this end, appropriate electromechanical or mechanical means are provided to adjust the angle of orientation of mirror 24 (or alternatively CRT 20 when mirror 24 is stationarily disposed in housing 18) whenever the angle of orientation of transducer 22 is adjusted. By way of example and not limitation, one such means is illustrated in FIG. 4.

The angle adjustment means 44 of FIG. 4 comprises three toothed gears 46, 48 and 50. Gear 46 rotates about a shaft 52 which is connected to both rotatable knob 42 and transducer 22. Accordingly, the angle of transducer 22 will be adjusted by an angle equivalent to the angular adjustment of rotatable knob 42. By providing an indicator position on knob 42 and an angular scale on wall 30 about the periphery of knob 42, it is possible to provide a visual indication of the angular orientation of transducer 22.

The teeth of gear 46 mesh with the teeth of gear 48 which is rotated about a stationary shaft 54. The ratio of the diameter of gears 46 and 48 is preferably 1:2 in order to ensure that the angular rotation of gear 48, responsive to the angular rotation of gear 46, is one half that of gear 46. The teeth of gear 48 mesh with the teeth of gear 50 causing gear 50 to rotate responsive to and in the same direction as gear 46. The diameter of gears 48, 50 are preferably equal to ensure that gear 50 rotates in the same direction as but one half the angle of gear 46.

Gear 50 is mounted on a shaft 56 which is connected to mirror 24 and controls the angular orientation thereof. Accordingly, mirror 52 will rotate in the same direction as, but one half the angle of, transducer 22 whenever knob 42 is rotated. In summary, the angle of orientation of both transducer 22 and mirror 24 with respect to housing 18 is adjusted by adjusting the angular orientation of rotatable knob 42. Significantly, the knob 42 adjusts the relative angular orientation of transducer 22 and mirror 24 in such a manner that the angle between the viewing face 38 of CRT 20 and the mirror 24 is at all times equal to the angle between the mirror 24 and the ultrasonic beam 40 generated by transducer 22. As a result of this limitation, the image display box 12 gives the physician the illusion that he is actually looking into the patient's body along a section corresponding the plane of the ultrasonic signals.

This phenomena can best be understood with reference to FIG. 2. As shown therein, the Doctor D looks into the viewing window 36 and partially observes the portion of the body of the Patient P over which the image display box is located through the half silvered mirror 24. At the same time, the Doctor sees the Raster image of the ultrasonic scan which is produced by the CRT 20 and reflected off the mirror 24. Since the angle $\theta$ between the mirror and the display face 38 of the CRT 20 is equal to the angle $\phi$ between the mirror 24 and the sonic beam 40, he gets the impression that he is actually looking into the patient's body along the plane defined by the sonic beam 40. As a result, the physician need not interpret what position the probe is actually scanning within the body of the patient, since the optics of the image display box 12 provide him with this information.

Returning again to FIG. 1, the transducer 22 is electrically connected to an appropriate electronic processing circuit 14 which serves both to energize transducer 22 and to process the ultrasonic echo signals received thereby. Appropriate electronic processing circuits are well known in the art and the particular processing circuits do not form part of the present invention. Accordingly, these circuits will not be discussed further herein.

Electronic processing circuit 14 is also electrically coupled to scan converter 16 and provides scan converter 16 with both the processed ultrasonic echo signals received by transducer 22 and the scan converter control signals required to write the echo information into the scan converter 16 and to read the stored information out of the scan converter 16 in the form of video signals which are applied to the control plates of CRT 20. The preferred scan converter 16 and the method for storing and converting the processed ultrasonic echo signals are described in some detail in U.S. Pat. No. 4,099,179 which has been incorporated herein by reference. Briefly, the foregoing patent discloses a method and system of electronic image storing and display of slow scan incoming signals. An electro-acoustic transducer assembly transmits a signal into the medium under investigation (normally the patient). Sound echoes are reflected from the areas in the medium which are denser than the ambient environment. These echoes are returned to the transducer and are transformed into electrical signals which are suitably written on the target of a storage tube. These written signals are read out by a IV Raster scan read signal so that the scene scanned by the probe can be viewed on the TV display.

In order for the sonic waves produced by transducer 22 to penetrate through the human body, be reflected and return to the probe, a time period of as long as 500 microseconds is necessary in order to ensure that the information from the points furthest away from the probe are received. If a very clear picture is desired, it is necessary to generate approximately 500 sonic signals in a single scan of the body. As a result, it is possible to generate only approximately 5 sonic scans per second. Since a minimum frame rate of 30 frames per second is required to produce an acceptable flicker, it is necessary to read the echo information out of the storage tube at a rate approximately six times the rate at which information is being read into the storage tube. Accordingly, each frame of ultrasonic echo information is read out of the storage tube approximately six times. For this reason, an essential component of the scan converter 16 is a storage tube or other electrical storage medium. When using a storage tube, the scan converter accepts the incoming processed echo signals (in electronic form) and writes on the surface of the storage tube in a format which matches the beam direction or "vector" of the original ultrasound energy beam. The returning echoes are written on the storage tube in their correct position and intensity corresponding to the position and reflectance of the original targets. Following the completion of the writing of the stored image, the storage tube beam then converts the stored information to a Raster scan format in order to enable one to read the image out to an ordinary Raster scan TV display (CRT 20). In the foregoing patent, the time periods in which information is written into the storage tube and read out of the storage tube are time multiplexed. Particularly, during alternate horizontal TV lines within the same field of the cathode ray tube, the scan converter is switched between the writing mode and the reading mode. Because there are an odd number of horizontal TV lines between successively generated ultrasonic beams, the sum of the echoes from two successively generated ultrasonic beams produce a complete composite ultrasonic sound wave form extending between the two consecutive ultrasonic beams. That is, those portions of the ultrasonic echo signals which are deleted during the reading period of a first ultrasonic echo signal are "filled" by the immediately succeeding ultrasonic echo signal. Thus, a form of ultrasonic or slow scan line segment interlaced is obtained with a resultant improvement in the picture viewed on CRT 20.

The storage tube described in the foregoing patent is operated in the non-destructive read-out mode. Accordingly, it was necessary to utilize a separate erase beam, just prior to the generation of each successive write beam, to remove the stored information from the storage tube. While this system has been found to be suitable in many applications, its use is somewhat limited. In order to obtain satisfactory results, it is necessary to provide appropriate circuitry to ensure that the erase beam just slightly proceeds the new write beam and to ensure that the areas traversed by the erase beam correspond to those locations on the storage tube onto which the last echo image was written. If appropriate circuit is not provided, the new input information will be interlaced with the previously stored information and an unsuitable CRT output will be obtained.

It is possible to omit the foregoing circuitry by operating the storage tube in a destructive read-out mode of operation. In this mode of operation, the intensity of the signal stored on the storage tube will automatically be reduced each time the read beam scans the face of the tube. By properly adjusting the capacitance of the insulative areas of the storage tube (as by reducing the thickness of the insulative material) and properly adjusting the magnitude of the read beam, it is possible to control the percentage of decay of the stored image during each scan of the read beam. By properly adjusting these parameters, it is possible to ensure that the stored information is substantially erased by the time new echo information is to be read onto the tube. By way of example, the stored information may be 70% erased by the time it is to be replaced with new echo information. By following this procedure, it is no longer necessary to generate a separate erase beam and a suitable CRT output is provided. The parameters which control the rate at which stored information is erased during the read operation is reviewed in B. Kazan and M. Knoll, "Electronic Store Image Storage" pp. 116–120.

The present invention may be embodied in other specific forms without departing from the spirit or essential attributes thereof and, accordingly, reference should be made to the appended claims, rather than to the foregoing specification as indicated in the scope of the invention.

What is claimed is:

1. An ultrasonic imaging system, comprising:
   a housing having a viewing window formed therein;
   a cathode ray tube mounted in said housing, said cathode ray tube including a generally planar viewing face lying in a first plane;
   a planar mirror mounted in said housing and lying in a second plane, one of said mirror and cathode ray tube being pivotally mounted such that the angle between said first and second planes is adjustable;
   a transducer pivotally mounted in said housing;
   electronic circuit means for causing said transducer to generate a succession of ultrasonic beams which propagate along a third plane, said electronic circuit means also for processing ultrasonic echo signals received by said transducer and for causing said cathode ray tube to display a real time raster type image corresponding to the information contained in said ultrasonic echo signals; and
   angle adjustment means for adjusting the angle of said third plane with respect to said housing, said angle adjustment means also for maintaining the angle between said second and third planes equal to the angle between said first and second planes when said angle of said third plane is changed with respect to said housing.

2. The ultrasonic imaging system of claim 1 wherein said cathode ray tube is stationarily mounted in said housing and said mirror is pivotally mounted in said housing.

3. The ultrasonic imaging system of claim 2 wherein said transducer is an elongated bar having a plurality of individual transducers embedded therein.

4. The ultrasonic imaging system of claim 2 wherein said transducer is a single transducer and wherein said imaging system further includes means for mechanically pivoting said transducer at a rapid rate such that said ultrasonic beams generated by said transducer propagate radially along said third plane.

5. The ultrasonic imaging system of claims 1, 2 or 3 wherein said angle adjust means comprises:
   a first gear mounted for rotation with said transducer;
   a second gear in operative engagement with said first gear such that said second gear rotates responsive to the rotation of said first gear;
   a third gear in operational engagement with said second gear such that said third gear rotates responsive to rotation of said first gear, said third gear mounted for rotation with said mirror, the relative diameters of said first, second and third gears being chosen such that said mirror is rotated in the same direction as but one half the angle of said transducer whenever the angle of orientation of said transducer is adjusted with respect to said housing.

6. The ultrasonic imaging system of claim 5 wherein said angle adjustment means further includes a rotatable knob located on the outside of said housing and in operative engagement with said first gear.

7. The ultrasonic imaging system of claims 1, 2 or 3 wherein said mirror is a half silvered mirror.

8. The ultrasonic imaging system of claim 7 wherein said housing includes a handle on either side thereof.

9. The ultrasonic imaging system of claim 1 wherein said electronic circuit means comprises:
   an electronic storage tube;
   write means responsive to said ultrasonic echo signals for writing ultrasonic echo information into said storage tube at first rate whereby new ultrasonic echo information is periodically stored in said storage tube at said first rate;
   read means for reading said stored information out of said storage tube and for applying appropriate biasing signals to said cathode ray tube in order to cause said cathode ray tube to display a real time Raster type image corresponding to the information read out of said storage tube, said read means reading said stored information out of said storage tube at a rate which is n times faster than the rate at which ultrasonic echo information is written into said storage tube by said write means, n being an inch greater than 1, such that each frame of ultrasonic echo information written into said storage tube is read out of said storage tube n times; and
   means for operating said storage tube in a destructive read mode wherein the stored information in said storage tube is substantially erased by the time new echo information is written into said storage tube.

10. The ultrasonic imaging system of claim 9 wherein said stored information is 70% erased by the time it is replaced with new echo information.

11. The ultrasonic imaging system of claim 9 wherein said ultrasonic echo information is divided into a plurality of scan lines and wherein sad Raster type image displayed on said cathode ray tube comprises a plurality of horizontal TV lines, the line rate of said scan lines being lower than the horizontal TV line rate of said cathode ray tube, said electronic circuit means further comprising:
   means for selecting said scan line rate to be an odd integer sub-multiple of said horizontal TV line rate;
   said write means writing said ultrasonic echo information into said storage tube in segments by writing each segment into said storage tube during the time required to scan one said horizontal TV line; and
   said read means reading said stored information out of said storage tube during the time required to scan the next said horizontal TV line to thereby write and read during alternate said horizontal TV lines of a single field of TV lines.

* * * * *